United States Patent [19]

Schneider et al.

[11] Patent Number: 4,759,753
[45] Date of Patent: Jul. 26, 1988

[54] EXTERNAL MALE URINARY CATHETER

[75] Inventors: Barry L. Schneider, Deerfield; Mahmood Mohiuddin, Lake Zurich, both of Ill.

[73] Assignee: Hollister Incorporated, Libertyville, Ill.

[21] Appl. No.: 941,203

[22] Filed: Dec. 12, 1986

[51] Int. Cl.⁴ ............................................. A61F 5/44
[52] U.S. Cl. ..................................................... 604/352
[58] Field of Search ............... 604/343, 345, 349–353; 285/260

[56] References Cited

U.S. PATENT DOCUMENTS

| | | | |
|---|---|---|---|
| 3,138,160 | 6/1964 | Stoutenburgh | 604/351 |
| 3,742,953 | 7/1973 | Lee | 604/352 |
| 3,835,857 | 9/1974 | Rogers et al. | 128/295 |
| 3,863,638 | 2/1975 | Rogers et al. | 128/295 |
| 4,581,026 | 4/1986 | Schneider | 604/352 |
| 4,588,397 | 5/1986 | Giacalone | 604/349 |
| 4,640,688 | 2/1987 | Hauser | 604/352 |

FOREIGN PATENT DOCUMENTS 2099706 10/1982 United Kingdom ............... 604/349
2125294A 3/1984 United Kingdom .

Primary Examiner—C. Fred Rosenbaum
Assistant Examiner—J. L. Kruter
Attorney, Agent, or Firm—Tilton, Fallon, Lungmus

[57] ABSTRACT

An external male catheter having an elastic sheath section and a receiving section connected together when the device is used as an external catheter but constructed to permit detachment of the receiving section, while retaining the sheath section in adhesive attachment to the wearer, to permit direct access to the urethral meatus for intermittent internal catherization.

13 Claims, 4 Drawing Sheets

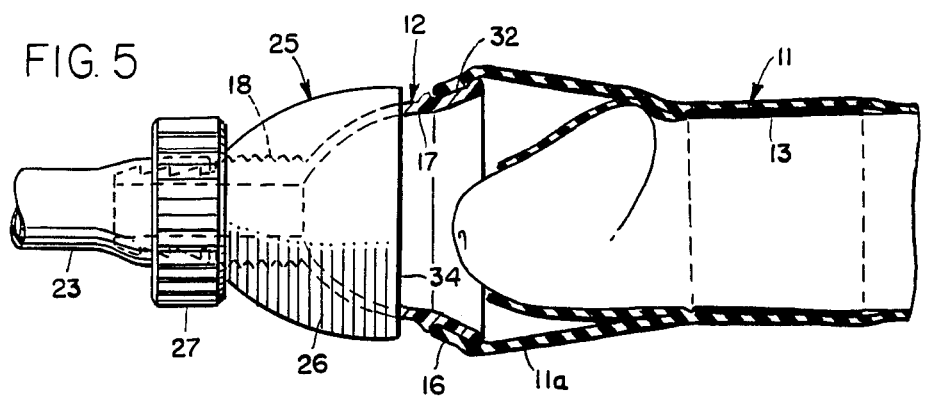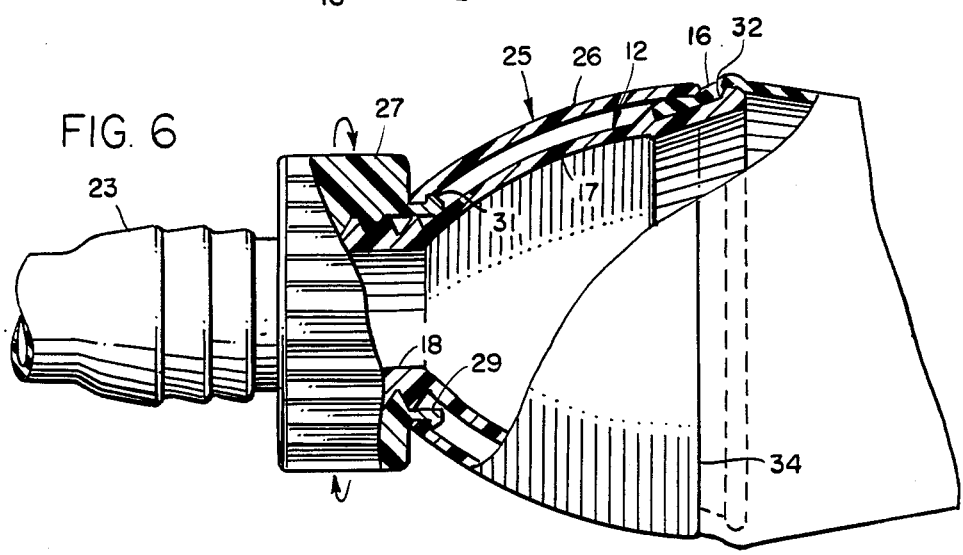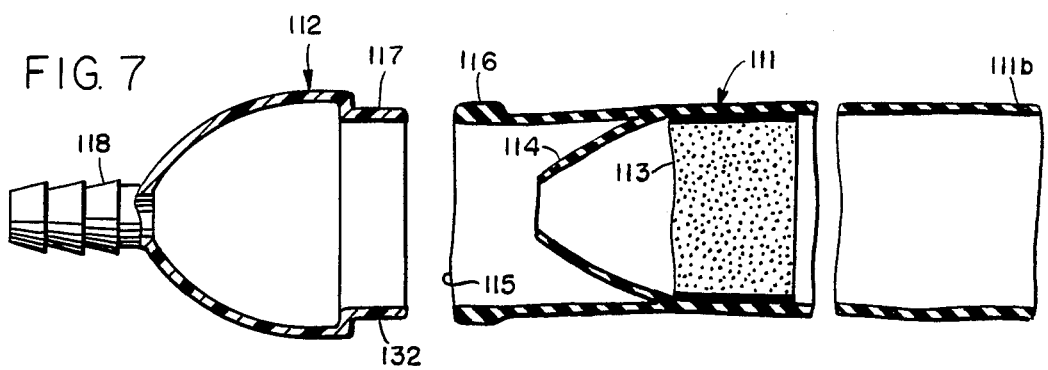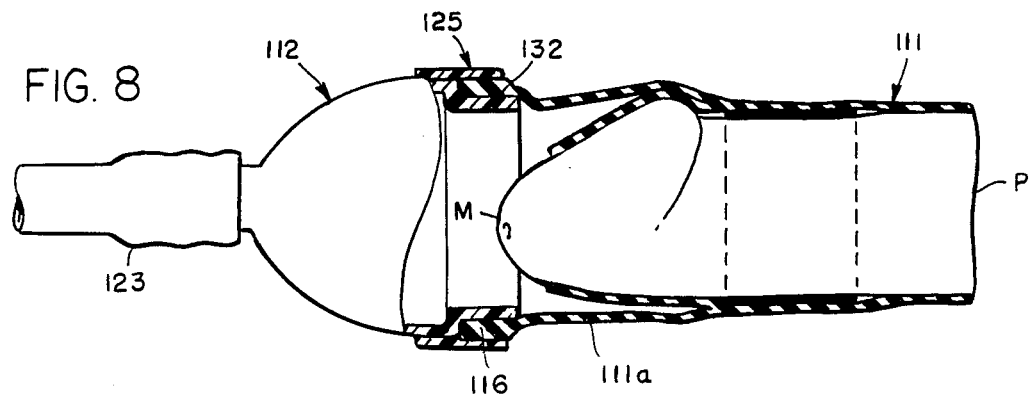

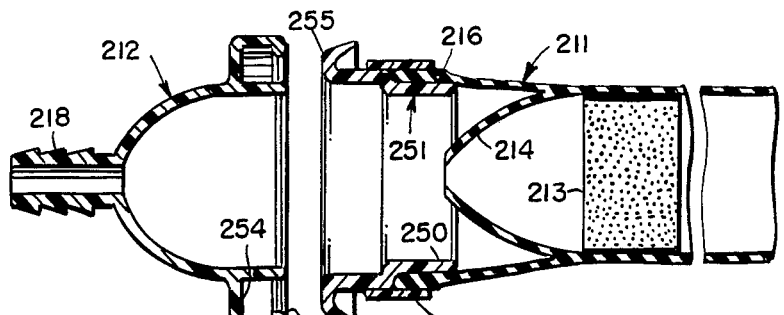
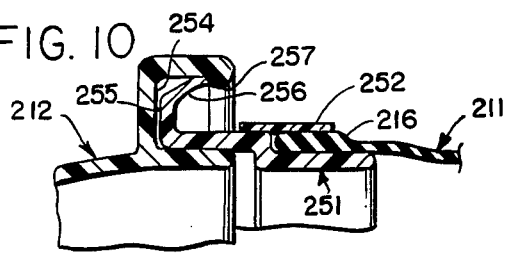
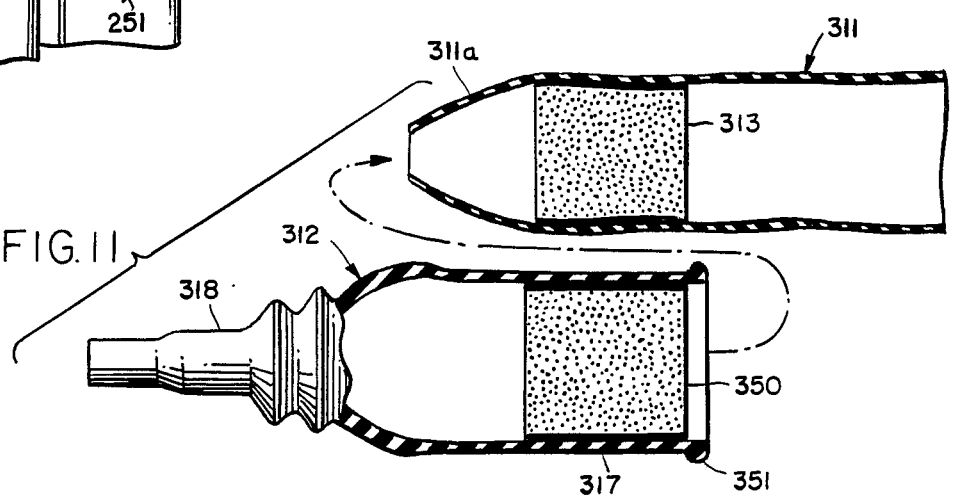
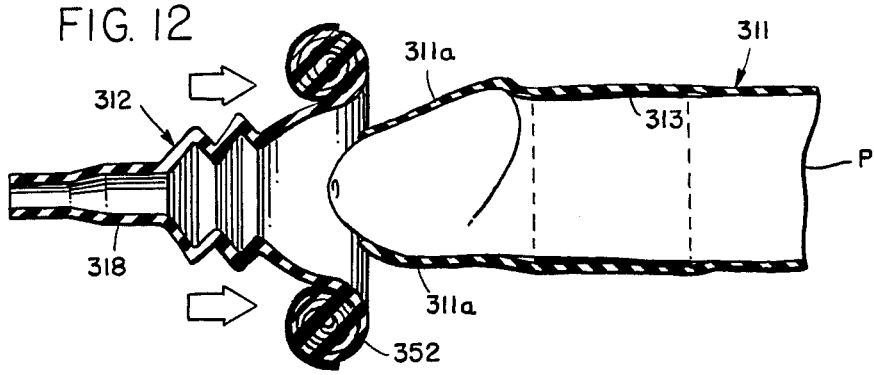
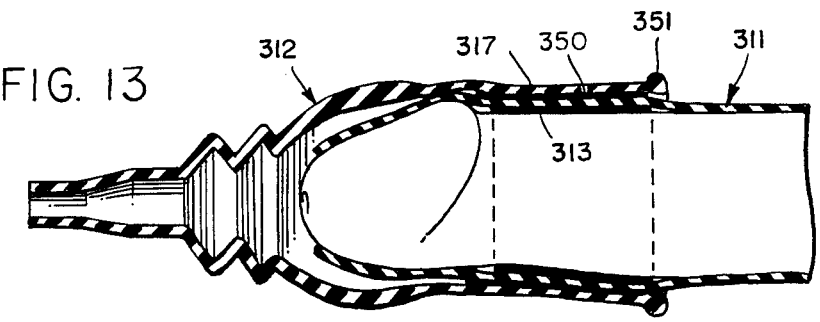

EXTERNAL MALE URINARY CATHETER

BACKGROUND AND SUMMARY

External male catheters generally take the form of an elastic penile sheath connected at its distal end to a drainage tube that, in use of the device, leads to a suitable collection receptacle. Such a catheter is typically held in place by a pad or coating of pressure sensitive adhesive as shown, for example, in U.S. Pat. Nos. 3,835,857, 3,863,638, and 4,178,851. One particularly effective sheath in widespread use is disclosed in U.S. Pat. No. 4,581,026. Such sheath has an inner sleeve that sealingly but non-adhesively engages the glans of a wearer's penis, the inner sleeve being held in position by a coating or pad of adhesive material in contact with the penile shaft behind the glans. Reference may also be had to U.S. Pat. No. 4,588,397 and British application No. 2,125,294A as further illustrations of the state of the art.

For certain types of incontinent patients, intermittent internal catherization is necessary to empty the bladder more completely and avoid complications that might develop from long-term retention of residual urine. For example, incontinent patients with spinal cord injuries frequently require such intermittent internal catherization. Such a procedure involves removing the external catheter to expose the urethral meatus and permit the insertion of an internal catheter for direct draining of the bladder. For a patient whose spinal injury is recent, such intermittent internal catherization may have to be performed as frequently as every three to four hours, but such intermittent internal catherization followed by replacement of an external catheter is believed preferable to leaving an internal catheter in place. Intermittent internal catherization nevertheless burdens the nursing staff, since the steps of removing an external catheter, introducing and removing an internal catheter, and replacing an external catheter are time consuming (therefore increasing the economic burden of the institution and, ultimately, the patient) and must be performed with care to reduce the possibilities of patient infection or injury. Even so, patient injury is possible because the frequent removal and replacement of adhesive-coated external catheters may irritate and even seriously harm sensitive skin surfaces. In efforts to avoid the problems caused by frequently removing and applying adhesively-coated external catheters, medical personnel in some institutions have instead wrapped straps or tape about the outsides of non-adhesive catheters to hold them in place, thereby confronting an even greater risk of strangulation and resulting vascular and tissue damage.

Accordingly, important aspects of this invention lie in recognizing this problem and in providing an external male catheter that permits intermittent internal catherization without the disadvantages described above. More specifically, the invention lies in providing an external catheter composed of two main sections—an elastic sheath section and a urine-receiving section—that are connected together when the device is in use but may be readily separated when internal catherization is required. Since the two sections are coupled together in close proximity to the urethral meatus, detachment of the urine-receiving section exposes the meatus for internal catheterization. Because only the urine-receiving section needs to be removed, the sheath section and its adhesive attachment to the penile shaft may remain undisturbed. Following internal catherization, the urine-receiving section (either the original component or a fresh replacement) may be reconnected to the sheath section to return the external catheter to an operative state.

Several forms of two-section external catheters are disclosed herein. In all constructions, the catheter includes at least two sections, one section taking the form of an elongated tubular sheath of thin, stretchable, elastic material dimensioned to be fitted upon and extend along the shaft of a patient's penis. Such a sheath section has proximal and distal ends with the latter terminating in a distal opening located in close proximity to the urethral meatus when the sheath section is worn by a patient. Adhesive means, preferably an internal coating of pressure sensitive adhesive, secures the sheath section to the penile shaft behind the glans. Ideally, the sheath section includes a non-adhesive portion that is stretched over the glans just behind the urethral meatus to protect the glans against injury that might otherwise be occasioned by prolonged contact with residual amounts of urine that are often retained within an external catheter.

Each embodiment also includes a tapered tubular receiving section having a proximal end portion with an enlarged opening and a distal portion adapted for connection to a drainage tube. Connecting means releasably join the proximal end portion of the receiving section to the sheath section to permit selective detachment of the receiving section when access to the urethral meatus is required for internal catherization. In one embodiment the receiving section is formed of flexible but still fairly stiff (i.e., semi-rigid) plastic material and the distal end of the sheath section is clamped between the receiving section and an external cup-shaped clamping member. In another form the receiving section is again composed of relatively rigid plastic but the clamping member comprises a removable pressure-sensitive adhesive strip that performs the dual functions of holding the proximal end of the sheath section in fluid-tight contact with the receiving section and adhesively connecting the two sections together. A further embodiment utilizes a pair of coupling rings, and other forms involve no rigid clamping or coupling elements but rely entirely on an adhesive connection between the two sections.

DRAWINGS

FIG. 5 is a longitudinal sectional view illustrating a first step in attaching the urine-receiving section to the distal end of the sheath section.

FIG. 6 is an enlarged and fragmentary longitudinal sectional view illustrating the final step of detachably securing the sheath section and receiving section together.

FIG. 7 is an exploded longitudinal sectional view showing the sheath section and receiving section of an external catheter constituting a second embodiment of the invention.

FIG. 8 is a longitudinal view, partly in section, showing the components of the second embodiment in fully assembled condition.

FIG. 9 is an exploded longitudinal sectional view of a third embodiment of the invention.

FIG. 10 is an enlarged fragmentary sectional view showing the coupling rings of the catheter sections of FIG. 9 in assembled condition.

FIG. 11 is a longitudinal sectional view showing the two sections of an external catheter constituting a fourth embodiment of the invention.

FIG. 12 is a longitudinal sectional view showing the sheath section in place on a wearer and illustrating a first step in the attachment of the urine-receiving section.

FIG. 13 is a longitudinal sectional view showing the external catheter of the fourth embodiment fully attached to a wearer.

DETAILED DESCRIPTION OF PREFERRED EMBODIMENTS

Figure 1:
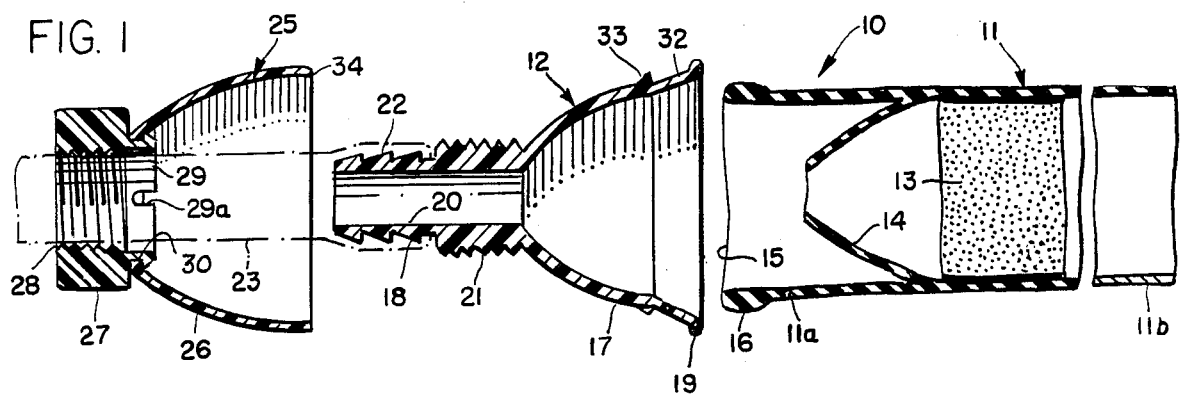
FIG. 1 is a longitudinal sectional view of an external catheter embodying this invention, the elements of the catheter being shown in exploded relation for clarity of illustration.
Figure 2:
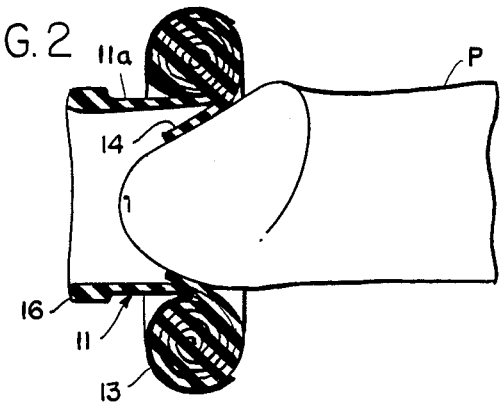
FIG. 2 is a sectional view illustrating a first step in attaching the sheath section of the catheter of FIG. 1.
Figure 3:
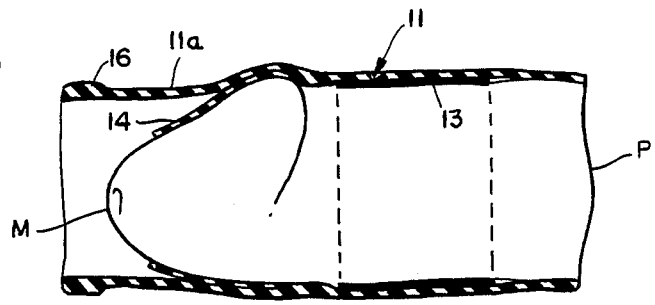
FIG. 3 is a sectional view illustrating the sheath section in place.

Referring to FIGS. 1-6, the numeral 10 generally designates an external catheter comprising a sheath section 11 and a receiving section 12. The sheath section is formed of latex or other highly stretchable, elastic material and, as indicated in FIG. 1, is of elongated cylindrical configuration. The thin sheath section should be dimensioned so that in slightly stretched condition it will fit comfortably about a patient's penis P with the distal portion 11a of the sheath section in close proximity to, and preferably just distal to, the urethral meatus M (FIG. 3). The sheath extends rearwardly or proximally along the shaft of the penis, terminating in a proximal end portion 11b. Adhesive means in the form of an annular coating 13 about the inside of an intermediate portion of the sheath section functions to hold the sheath section in place upon the wearer. While an internal adhesive coating of any suitable pressure sensitive adhesive (such as a medical-grade acrylic adhesive) is preferred, it is to be understood that the retention means may also take the form of a pad or strip of adhesive material that is not a part of the sheath section but is instead applied separately to the penile shaft. Such an alternative is well known as disclosed, for example, in U.S. Pat. No. 4,581,026.

Preferably, the sheath section 11 includes an integral inner sleeve 14 located within the distal portion of the sheath in front of (or distal to) adhesive coating 13. The advantages such an inner sleeve are described in U.S. Pat. No. 4,581,026, the disclosure of which is incorporated by reference herein. In such a construction, adhesive coating 13 functions primarily as retention means for holding the inner sleeve 14 in stretched condition over a major portion of the skin surface of the glans of penis P (FIG. 3). The stretched sleeve forms a protective sealing function without making adhesive contact with the glans, since the only adhesive contact between the sheath section and the penis occurs along the penile shaft behind the glans. The adhesive annulus 13 thus keeps the entire sheath section 11 from slipping forwardly to reduce the tension and non-adhesive sealing effect of the stretched inner sleeve 14.

Sheath section 11 has a large opening 15 at its distal end 11a and, as shown clearly in the drawings, the thickness of the elastic material at the extreme distal end is increased to provide an annular rim or bead 16.

The urine-receiving section 12, which may be referred to simply as the receiving section, is formed of polyethylene, polypropylene, or some other semi-rigid plastic material. As shown in FIG. 1, the receiving section is generally funnel-shaped with an enlarged and generally frusto conical proximal portion 17 and a reduced tubular distal portion 18. The proximal portion has a relatively large opening or mouth 19 and the distal portion has a lumen or passage 20 extending axially therethrough and communicating with the mouth of the proximal portion. External threads 21 extend along part of the distal portion 18 and a series of annular ribs 22 may be provided near the distal end of that portion for retaining a drainage tube 23. The drainage tube is entirely conventional, may be formed of latex or other suitable material, and leads to a suitable urine-receiving receptacle (not shown).

The connecting means for detachably connecting the two sections together includes a clamping member 25 which has a cup-shaped proximal portion 26 and a distal neck portion 27. The neck portion has an internally threaded bore 28 which communicates with the interior of the cup section and which slidably receives the flexible drainage tube 23. For reasons that will become apparent shortly, the neck portion 27 and cup-shaped portion 26 are preferably formed as separate elements that are coupled together in a way that prevents axial separation but permits relative rotation. For that purpose, the neck portion 27 has a proximal annular collar 29 which projects through a distal opening 30 in the end of cup-shaped portion 26, the collar having a terminal shoulder 31 that bears against the inner surface of the cup-shaped portion and maintains the two parts in assembled condition. To facilitate initial assembly, collar 29 may be provided with one or more recesses 29a (FIG. 1) to permit slight inward displacement of the walls of the collar when the collar is inserted into the opening 30 of cup-shaped portion 26.

As shown clearly in FIGS. 5 and 6, the cup-shaped portion 26 is dimensioned to receive the enlarged proximal portion 17 of receiving section 12 when the neck portion 27 of the clamping member is threaded upon the distal portion 18 of the receiving section. At its larger end, the proximal portion 17 of the receiving section has a sloping (frusto-conical) outer surface 32 that supports the bead 16 of the sheath section when the distal portion of the sheath section is stretched about the proximal end of receiving section 12 (FIGS. 5 and 6). An annular stop 33 may be provided to limit the extent of distal sliding movement of the bead on surface 32.

Figure 4:
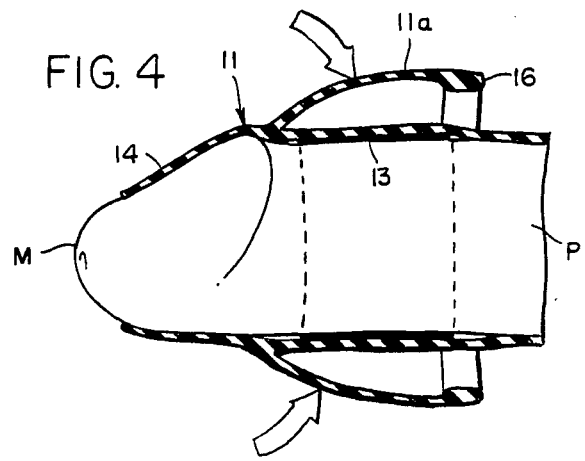
FIG. 4 is a sectional view illustrating the step of everting the distal end portion of the sheath section.

FIGS. 2-6 illustrate the steps of attaching the external catheter to a wearer. The sheath section is preferably marketed in the rolled condition depicted in FIG. 2 and is applied by urging the inner sleeve 14 against the glans to cause a stretching of the sleeve. Thereafter, the sheath section is unrolled to bring adhesive 13 into contact with the penile shaft directly behind the glans (FIG. 3). Access to the urethral meatus M for purposes of internal catherization can be readily achieved by folding or everting the distal portion 11a as shown in FIG. 4. Such everting of the distal portion is also helpful as an initial step in fitting the rim or bead 16 about the enlarged end of receiving section 12. Once the bead is stretched into place, the clamping member 25 is shifted in a proximal direction, by rotating the threaded neck portion 27, to force the rim 34 of the cup-shaped portion 26 into tight sealing contact with bead 16 (FIGS. 5, 6).

When access to the urethral meatus is required for purposes of internal catherization, neck portion 27 is simply unthreaded to retract the clamping member 25 and permit the bead 16 to be removed from the supporting surface or channel 32 of receiving section 12. As already indicated, access may be further increased by folding the distal portion 11a of the sheath section in a reverse direction (FIG. 4). When internal catherization is completed, the receiving section 12 (either the original receiving section or a fresh replacement) may again be attached to the sheath section 11 in the manner already described.

FIGS. 7 and 8 illustrate a second embodiment in which the sheath section 111 may be identical to section 11 of the first embodiment. Receiving section 112 may also be formed of a relatively rigid plastic material and, as shown in FIG. 7, has a proximal end portion 117 and a distal end portion 118. The proximal end portion has an outer proximal surface 132 of larger diameter than the untensioned inside diameter of opening 115; therefore, bead 116 of the sheath section must be stretched to fit the two parts together as shown in FIG. 8. Thereafter, clamping or retaining means in the form of a strip of cloth or plastic adhesive-coated tape 125 is wrapped about the receiving section 112 and bead 116 to hold the bead tightly against surface 132 and to connect the bead and receiving section together. When detachment of the sections is required for internal catherization, tape 125 is simply removed, bead 116 is slipped off of surface 132, and the distal portion 111a of the sheath section 111 is (if necessary or desired) folded in a reverse direction as previously described in connection with FIG. 4. Following internal catherization, the receiving section 112, or a fresh replacement, may be reattached to sheath section 111.

In the embodiment of FIGS. 9 and 10, sheath section 211 may again be identical to sheath sections 11 and 111. However, bead 216 is stretched about the neck portion 250 of a first coupling ring 251. Adhesives or any other suitable means may be provided for permanently securing the coupling ring and bead together. In the illustration given, a band 252 of pressure-sensitive adhesive tape is wrapped tightly about the neck portion and bead to hold the parts together.

The receiving section 212, like the receiving sections already described, may be formed of relatively rigid plastic material. At its enlarged proximal end, the receiving section is provided with an integral second coupling ring 253 constructed to mate with the first coupling ring 251. The mechanical interconnection between the two coupling rings may be any of a variety of interconnections well known in the closure art and used on other types of medical devices. In the illustration given, coupling ring 253 has an axially-facing channel 254 for receiving the head 255 of ring 251. The head includes a flexible sealing-latching element 256 which engages the inner surface of the channel 255 and also bears against bead 257 at the entrance to that channel (FIG. 6). For further details concerning such a mechanical coupling, reference may be had to U.S. Pat. No. 4,419,100.

In the embodiment of FIGS. 11–13, the sheath section 311 has a tapered distal portion 311a that is similar in shape, size, and function to the inner sleeves 14, 114, 214 of the prior embodiments. Directly behind the tapered distal portion, the sheath section is preferably internally coated with a layer of adhesive 313. Like the sheaths of the prior embodiments, sheath section 311 is formed of latex or other highly stretchable elastic material.

The receiving section 312 is also formed of latex or other stretchable, elastic material and, as shown in FIG. 11, is tubular with a generally cylindrical proximal end portion 317 and a reduced distal end portion 318. The distal portion may be attached to a drainage tube leading to a suitable urine-collecting receptacle (not shown).

The inner surface of the enlarged proximal end portion 317 is coated with a layer of pressure-sensitive adhesive 350 (FIG. 11). Preferably, the extreme proximal end of the receiving section is also provided with a bead or annular rib 351. In a form made available to users, the receiving section 312 should have its proximal end portion rolled to form a torus 352 as illustrated in FIG. 8. The sheath section 311 would be similarly rolled prior to application and, when fitted upon a patient, would appear as shown in FIG. 12 with the tapered distal portion 311a stretched over the glans and with adhesive layer 313 in contact with the penile shaft directly behind the glans. The receiving section is fitted in place simply by unrolling it over sheath section 312 so that the adhesive coating 350 generally circumscribes the area in which annular adhesive layer 313 is located (FIG. 13). To remove the receiving section 312, the proximal end portion of that section is simply peeled or rolled forwardly (bead 351 may be gripped for that purpose) to break the adhesive connection between the two sections. Following internal catherization, a fresh receiving section may then be fitted upon the patient.

Figure 14:
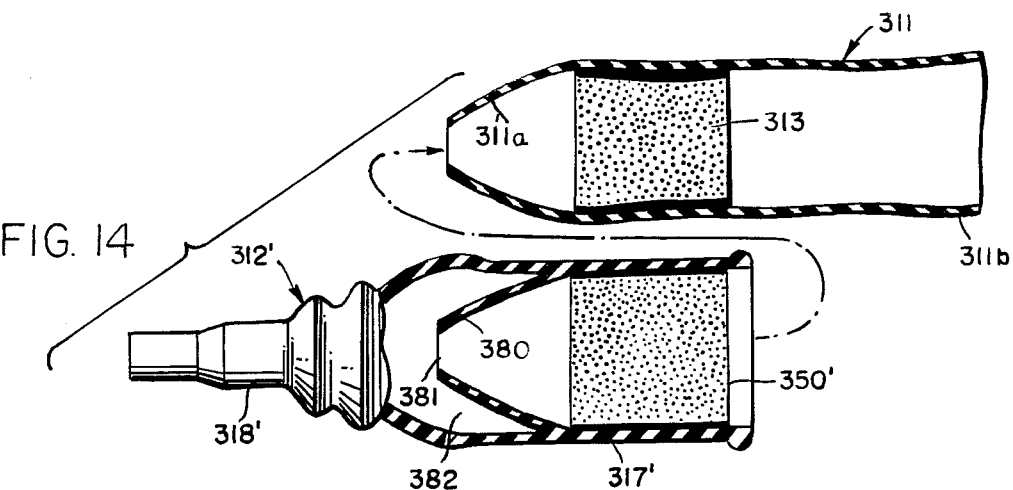
FIGS. 14 and 15 are longitudinal sectional views showing a catheter having a sheath section similar to that of FIGS. 12 and 13 but having a modified urine-receiving section.
Figure 15:
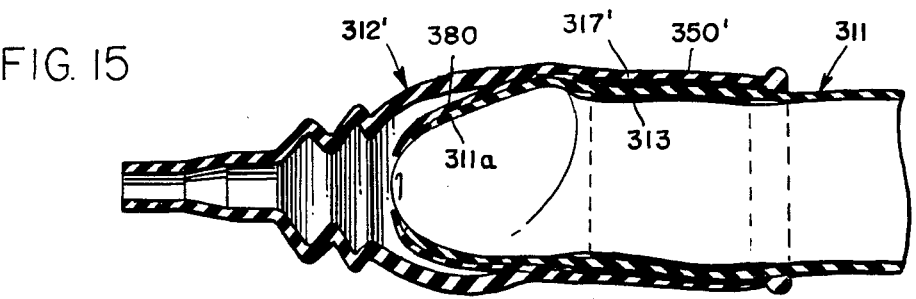

The embodiment of FIGS. 14 and 15 is identical to the version depicted in FIGS. 11–13 except for a modification of urine-receiving section 312'. Receiving section 312' includes the same reduced distal end portion 318', enlarged proximal end portion 317', and internal adhesive coating 350'. However, unlike the receiving section of the preceding embodiment, section 312' also includes an integral inner sleeve 380 that tapers forwardly (distally) and inwardly within the interior of the receiving section just distal to adhesive coating 350'. The inner sleeve portion 380 terminates in a reduced opening 381 within the interior 382 of the receiving section.

Each of the sections 311 and 312' may be rolled prior to application and, when fitted upon a patient, would appear as shown in FIG. 15 with the tapered sleeve portion 380 stretched over the distal portion 311a of the sheath section, both fitting snugly over the glans, and with the adhesive layer 313 in contact with the penile shaft directly beyond the glans and the adhesive coating 350' surrounding the area of the sheath section that is adhesively secured to the penile shaft. The advantage of such a construction is that the adhesive coating 350' is protected against fluid contact should a surge of urine discharged into the receiving section 312' result in momentary expansion of that section and fluid back up within the interior 382 of section 312'. Should back pressure develop, it would instead tend to urge the inner sleeve 380 of the receiving section 312' into even tighter engagement with the distal portion 311a of the sheath section 311, and that distal portion would in turn be urged into tighter sealing engagement with the glans about which it is stretched.

Figure 16:
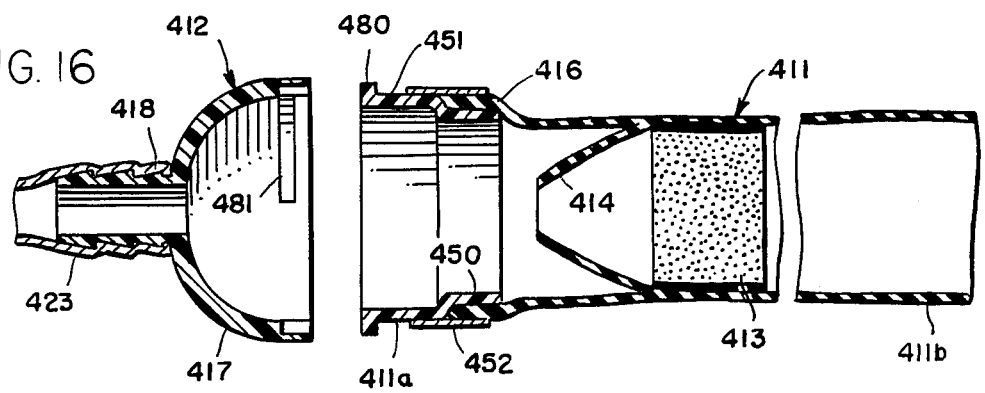
FIG. 16 is an exploded longitudinal sectional view showing the sheath and receiving sections of a catheter constituting a further embodiment of the invention.
Figure 17:
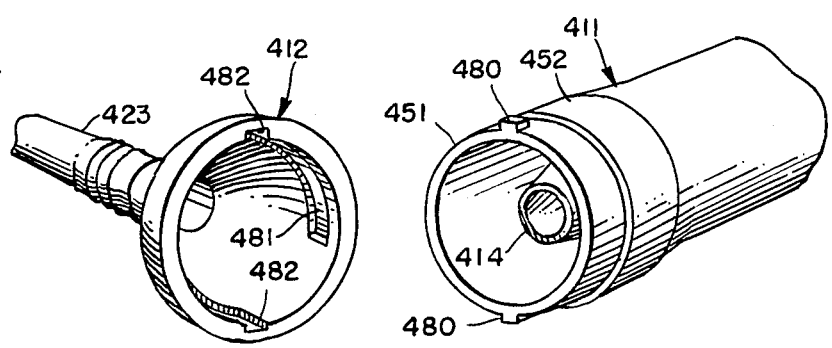
FIG. 17 is a perspective view showing the coupling construction for the sheath and receiving sections of the form depicted in FIG. 16.

The embodiment of FIGS. 16 and 17 is similar to that of FIGS. 9 and 10 except for differences in the mechanism for detachably coupling sheath section 411 to urine-receiving section 412. Like sheath section 211, section 411 has distal and proximal end portions 411a and 411b, respectively, an inner sleeve 414, and an adhesive means in the form of an internal annular adhesive coating 413. Bead 416 of the sheath section is stretched about the neck portion 450 of a first coupling ring 451. A band 452 of pressure-sensitive adhesive tape is wrapped tightly about the neck portion and bead to hold the parts together, but it is to be understood that any other means for permanently and sealingly joining the parts together may be used.

The receiving section 412, like the receiving sections previously described, is formed of relatively rigid plastic material. The reduced distal portion 418 of the receiving section may be connected to a flexible drainage tube 423. The enlarged annular proximal portion 417 functions as a coupling ring for detachably joining the receiving section to ring 451 of the sheath section. The coupling takes the form of a bayonet connection, with two or more circumferentially-spaced and outwardly-projecting lugs 480 of the coupling ring 451 being received in internal arcuate slots or grooves 481 of receiving section 412. The lugs are inserted into, and removed from, the grooves through axis openings 482, shown most clearly in FIG. 17. The bayonet connection essentially functions as a screw connection requiring only a partial turn for attachment and detachment, and it will be understood that, if desired, the proportions of the parts may be altered to provide conventional screw threads between the sections.

While in the foregoing we have disclosed embodiments of the invention in considerable detail for purposes of illustration, it will be understood by those skilled in the art that many of these details may be varied without departing from the spirit and scope of the invention.

We claim:

1. An external male urinary catheter comprising an elongated tubular sheath of thin, stretchable, elastic material dimensioned to be fitted upon and extend along the shaft of patient's penis; said sheath section being generally cylindrical in shape and having proximal and distal end portions; said distal end portion terminating in a distal opening located in close proximity to the urethral meatus when said sheath section is worn by a patient; said opening having a diameter at least as large as the inside diameter of said sheath section when said sheath section is in an unstretched state; adhesive means for adhesively securing said sheath section to the penile shaft; a tapered tubular receiving section having a proximal end portion with an enlarged opening and a distal portion adapted for connection to a drainage tube; said receiving section being formed of relative rigid plastic material and said proximal end portion thereof having an outside diameter larger than the inside diameter of said sheath section in an unstretched state; and means releasably connecting the proximal end portion of said receiving section to said sheath section for selective detachment of said receiving section when access to the urethral meatus is required for internal catherization.

2. The catheter of claim 1 in which said sheath section includes a stretchable elastic inner sleeve disposed within said distal end portion and formed integrally therewith; said inner sleeve being dimensioned and arranged for sealingly but non-adhesively engaging the glans of a wearer's penis.

3. The catheter of claims 1 or 2 in which said sheath section has an integral annular bead of increased wall thickness about the opening at the distal end thereof.

4. The catheter of claims 1 or 2 in which said means for releasably connecting said receiving section to said sheath section comprises a first coupling ring of flexible plastic secured to said distal end of said sheath section; said receiving section being formed of flexible plastic and including a second coupling ring at its proximal end; said rings having interfitting contact portions for latching and sealingly engaging each other when said rings are coupled together.

5. The catheter of claim 4 in which said first coupling ring includes a neck portion extending into the distal end of said sheath section; and means securing said neck portion and distal end of said sheath section together.

6. The catheter of claim 5 in which said means for securing said neck portion and distal end of said sheath section together comprises an annular band of adhesive tape.

7. The catheter of claim 4 in which said interfitting contact portions of said coupling rings comprises at least one lug portion projecting from the outer surface of one of said rings and at least one internal groove provided by the other of said rings for receiving said lug portion when the lug-providing ring is urged into the groove-providing ring and the two rings are then rotated in relation to each other.

8. The catheter of claim 7 in which said interfitting contact portions constitute a bayonet connection.

9. The catheter of claims 1 or 2 in which said distal end portion of said sheath section is stretched about said proximal end portion of said receiving section when said sections are connected together; said connecting means including a clamping member extending about said distal end portion of said sheath section and detachably securing the same in place upon the proximal end of said receiving section.

10. The catheter of claim 9 in which said clamping member includes a proximal cup-shaped portion with a rim at its proximal end for engaging said distal end of said sheath section and clamping the same against said receiving section.

11. The catheter of claims 1 or 2 in which said distal end portion of said sheath section is stretched about said proximal end portion of said receiving section when said sections are connected together; said connecting means comprising a strip of pressure-sensitive adhesive tape extending about and adhesively engaging both said distal end of said sheath section and said proximal end of said receiving section.

12. An external male urinary catheter comprising an elongated tubular sheath of thin, stretchable, elastic material dimensioned to be fitted upon and extend along the shaft of a patient's penis; said sheath section having proximal and distal end portions; said distal end portion terminating in a distal opening located in close proximity to the urethral meatus when said sheath section is worn by a patient; adhesive means for adhesively securing said sheath section to the penile shaft; a tapered tubular receiving section having a proximal end portion with an enlarged opening and a distal portion adapted for connection to a drainage tube; means releasably connecting the proximal end portion of said receiving section to said sheath section for selective detachment of said receiving section when access to the urethral meatus is required for internal catherization; said sheath section having an integral annular bead of increased wall thickness about the opening at the distal end thereof; said receiving section being formed of relatively rigid plastic material and said proximal end portion being larger than the annular bead of said sheath section when said sheath section is in an unstretched state; said bead being stretched about said proximal end of said receiving section when said sections are connected together; said connecting means including a clamping member extending about said bead and securing the same in place upon said proximal end of said receiving section; said clamping member also including a tubular neck portion and a proximal cup-shaped portion with a rim at its proximal end for engaging said bead and clamping the same tightly against the proximal end of said receiving section; said neck portion being internally threaded and said distal end of said receiving section being externally threaded; said clamping member and receiving section being threadedly connected for urging said rim into tight clamping engagement with said bead of said sheath section.

13. The catheter of claim 12 in which said neck portion of said clamping member is rotatably connected to said cup-shaped portion to permit axially movement of said rim into and out of clamping engagement with said bead, upon rotation of said threaded neck portion, without concurrent rotation of said cup-shaped portion.

* * * * *